United States Patent [19]

Christensen et al.

[11] 4,004,586
[45] Jan. 25, 1977

[54] METHOD AND APPARATUS FOR SEALED, STERILE CONNECTION

[75] Inventors: John G. Christensen, Prairie View; Thomas R. Hektner, Wilmette; Steven L. Olson, Lake Zurich, all of Ill.

[73] Assignee: Baxter Travenol Laboratories, Inc., Deerfield, Ill.

[22] Filed: Mar. 12, 1975

[21] Appl. No.: 557,853

[52] U.S. Cl. ............ 128/214 D; 128/214.2; 222/83; 285/3; 285/260
[51] Int. Cl.² .................................. A61M 5/14
[58] Field of Search ....... 128/214 R, 214 D, 214 C, 128/214.2; 222/83; 285/3, 260

[56] References Cited
UNITED STATES PATENTS

| | | | |
|---|---|---|---|
| 2,726,656 | 12/1955 | Lockhart | 128/216 |
| 2,847,995 | 8/1958 | Adams | 128/214 R |
| 2,955,595 | 10/1960 | Semple | 128/214 D |
| 3,127,892 | 4/1964 | Bellamy et al. | 128/214.2 |
| 3,306,563 | 2/1967 | Soto | 128/214 R X |
| 3,327,709 | 6/1967 | Nehring et al. | 128/214 D |
| 3,902,489 | 9/1975 | Carter | 128/214 R |
| 3,909,910 | 10/1975 | Rowe et al. | 128/214 R X |

FOREIGN PATENTS OR APPLICATIONS

| | | | |
|---|---|---|---|
| 1,082,035 | 6/1954 | France | 128/214 D |
| 1,282,046 | 12/1961 | France | 128/214 D |
| 1,300,635 | 8/1969 | Germany | 128/214 R |

Primary Examiner—Dalton L. Truluck
Attorney, Agent, or Firm—Garrettson Ellis; Paul C. Flattery

[57] ABSTRACT

First and second sealed, sterile containers, having respectively communicating first and second fluid transfer tubes, the tubes having diaphragms occluding the bores thereof, may be connected together in sterile manner for the sterile transfer of the contents of one container to the other. To accomplish this, one point of a double-pointed, hollow spike is inserted into each of the bores of the fluid transfer tubes, at the free ends thereof, the spike being proportioned to tightly and sealingly fit into each bore of the fluid transfer tubes. Thereafter, the spike and that portion of the tubes extending from the diaphragms to the free ends thereof are sterilized. Then the points of the spike are moved to rupture the diaphragms, to open a flow channel, and the sterile contents are transferred. The fluid transfer tube of the container receiving the desired sterile contents is then resealed, prior to breaking sterility by opening the connection.

20 Claims, 6 Drawing Figures

METHOD AND APPARATUS FOR SEALED, STERILE CONNECTION

BACKGROUND OF THE INVENTION

Containers for blood, physiological solutions (such as parenteral solution or blood cell washing solution), or the like, are commonly used in a large variety of medical procedures. Usually, it is absolutely crucial that the blood or physiological solutions be retained in sterile manner. For example, once a conventional blood bag has been entered, following collection of the blood, it can no longer be stored, but must be used immediately to avoid the risk of catastrophic infection. Any significant delay may provide opportunity for microorganisms which have entered the blood or solution to multiply.

However, it would be desirable to obtain entry to the sterile contents of a container, while avoiding the risk of contamination, so that a portion of the sterile contents could be removed, or a medicament or other material added, and the resulting contents stored further for a few more days or weeks as desired.

For example, in cell washing procedures with the Travenol ELUTRAMATIC cell washing system, it is necessary to repeatedly draw aliquots of sterile cell washing solution from containers. At the present time, a large number of separate, small solution containers, must be used to preserve sterility, although it would be clearly more convenient to utilize a large container of parenteral solution by making repeated entries to the container, to remove the desired aliquots of solution.

In another aspect, it would be desirable to be able to obtain entry to sterile blood in a container, in order to withdraw only a portion of a blood unit. For example, a small child may need blood, but does not need a whole unit of blood. Also, one may wish to add medicaments, nutrients, or processing solutions to the blood; or to obtain access to blood components after the blood has been centrifuged, or the like.

In a third aspect, it is desirable in the field of hyperalimentation fluids (that is, feeding of a patient by means of a parenteral route) to mix protein solutions and carbohydrate solutions for administration of te mixture to the patient. However, it has been found that these solutions are extremely susceptible to bacterial growth, and thus, under current techniques, cannot reliably be stored without the danger of a rapid increase in bacterial contamination.

In accordance with this invention, a process and apparatus is provided for obtaining sterile access to the contents of a container, with such reliable sterility of access that the remaining contents may be further stored for essentially the same length of time as if no entry had been made to the container at all.

As a result of this, for the first time it becomes possible to make multiple entries into blood and solution containers without compromising the sterility, and without shortening the useful life of the contents of the container.

DESCRIPTION OF THE INVENTION

In accordance with this invention, a method is provided for transferring sterile contents from a first, sealed, sterile container, having a first, flexible, sealed fluid transfer tube, to a second, sealed, sterile container having a second, flexible, sealed fluid transfer tube. The first and second tubes communicate at one end thereof with their respective sealed, sterile containers. The first and second tubes also have a free end, and are each sealed with a diaphragm across their bores, the diaphragms being spaced from the free ends of the first and second tubes.

To practice this invention, a point of a double-pointed, hollow spike is inserted into each of the bores of the first and second tubes at the free ends thereof, but insufficiently far to rupture the diaphragms. The spike is proportioned to tightly and sealingly fit into each bore of the first and second tubes.

Thereafter, the spike, and that portion of the first and second tubes extending from their respective diaphragms to the free ends of the tubes, are sterilized, typically by dry heat sterilization sufficient to destroy all organisms. For example, a heat application of 250° C. for about 60 to 90 seconds has been found to be effective.

Following this, the first and second flexible sealed, fluid transfer tubes are axially moved relative to the spike, to cause the points of the spike to pass through the respective diaphragms. Accordingly, a flow channel is opened between the first and second containers. The sterile contents of the first container are then passed through the connected fluid transfer tubes to the second container.

Thereafter, prior to disconnection of the first and second fluid transfer tubes, and while sterility is retained, the second tube is resealed in any desired manner, for example by means of a HEMATRON heat sealing device, sold by the Fenwal division of Travenol Laboratories, Inc. Deerfield, Ill. The result of this is that the desired contents of the first container have been transferred to the second container through a completely sealed, sterile system. When properly done, there is no increased risk of contamination of the sterile environment.

Accordingly, the new contents of the second container may be stored for as long as corresponding material which was initially sterile-sealed, and has not been entered.

Preferably, clip members surround each of the fluid transfer tubes adjacent the free ends thereof, to prevent the axial collapsing and consequent rupturing of the diaphragm of each tube by the hollow spike.

After the sterilization step, the clip members are removed or otherwise disabled to permit the axial collapse and opening of the tubes to take place. The sterile fluid transfer tubes may define external flanges, against which the clip member may bear to prevent their axial collapse.

U.S. Pat. No. 3,127,812 discloses a container for blood having a sterile, sealed fluid transfer tube which contains a diaphragm and an internally mounted spike for rupture of the disphragm. The tube is separable adjacent the spike so that, after rupturing of the diaphragm and transfer of the desired contents, the tube may be separated for further transfer of contents to another container by use of the internal needle, which is by such separation exposed to the exterior.

It can be seen that this structure, although useful, does not permit the sterile transfer of contents between two initially separate, unconnected containers, which is a major purpose of the invention of this application.

Referring to FIGS. 1 through 4, a pair of blood bags 10, 12 are shown, each carrying a plurality of sealed fluid transfer tubes 14, 15, 16, 17, and 18. Each fluid transfer tube is terminated with a sealed tubular connector member 20, 21, 22, 23, and 24, each of similar construction. The connector members are adapted to carry a double-pointed spike 26, and may be delivered to the user with certain of the connector members having such spike in mounted position. Alternatively, the spike 26 may be kept separate from the connector members until they are desired for use.

Figure 3:
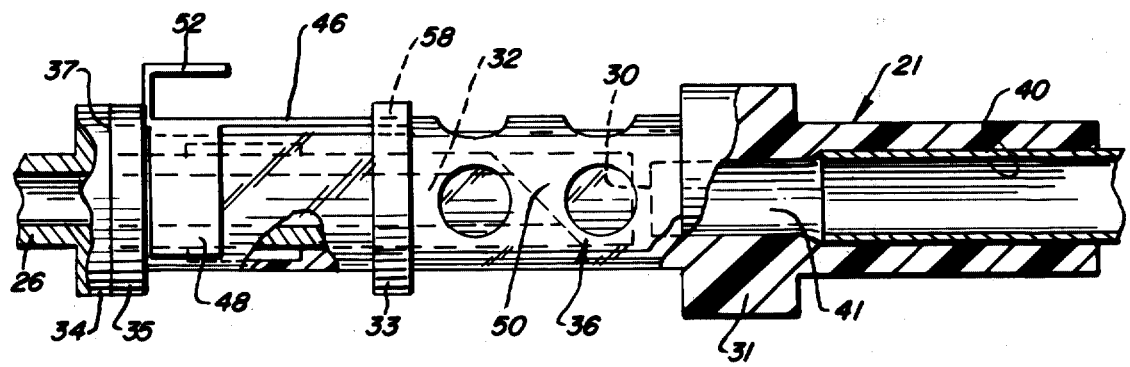
FIG. 3 is a further enlarged view, with portions broken away of a connector member of a fluid transfer tube of FIG. 1, and associated parts.
Figure 2:
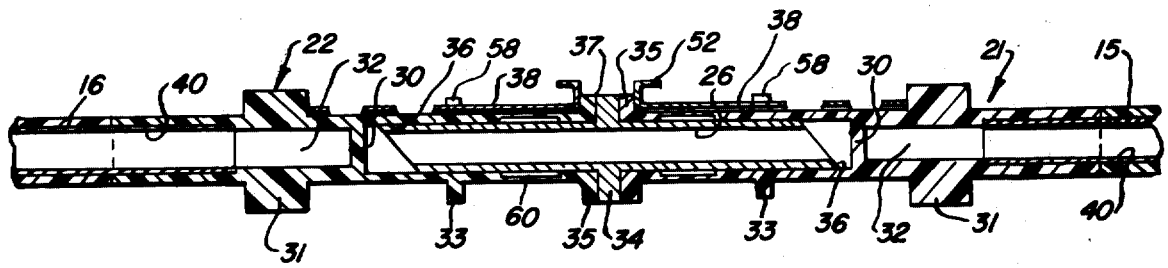
FIG. 2 is an enlarged view, taken in longitudinal section of the connection between two separate containers in accordance with this invention.
Figure 5:
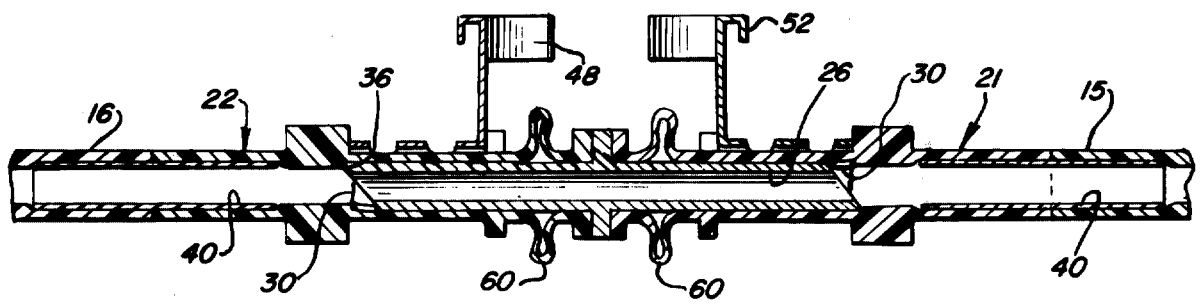
FIG. 5 is a longitudinal sectional view of the connection system as shown in FIG. 2, after the double-pointed spike has penetrated the diaphragms.

The connector members 20 through 24 may be made of silicone rubber tubing, and are each retained in communication with the remainder of fluid transfer tubes 14 through 18 by a rigid sleeve 40 (FIGS. 2 and 3). Sleeve 40 typically has an inner diameter equal to bore 41 to provide laminar, non-turbulent flow of blood therethrough, but has an outer diameter which is sufficiently larger to force a portion of each tubular silicone rubber connector member into an expanded relationship, to firmly anchor it on sleeve 40, as shown in FIGS. 2, 3 and 5. Correspondingly, the remaining portions of tubes 14 through 18, which may be conventionally made of vinyl plastisol, also are attached in an expanded relation on sleeve 40 for secure anchoring thereto.

Figure 1:
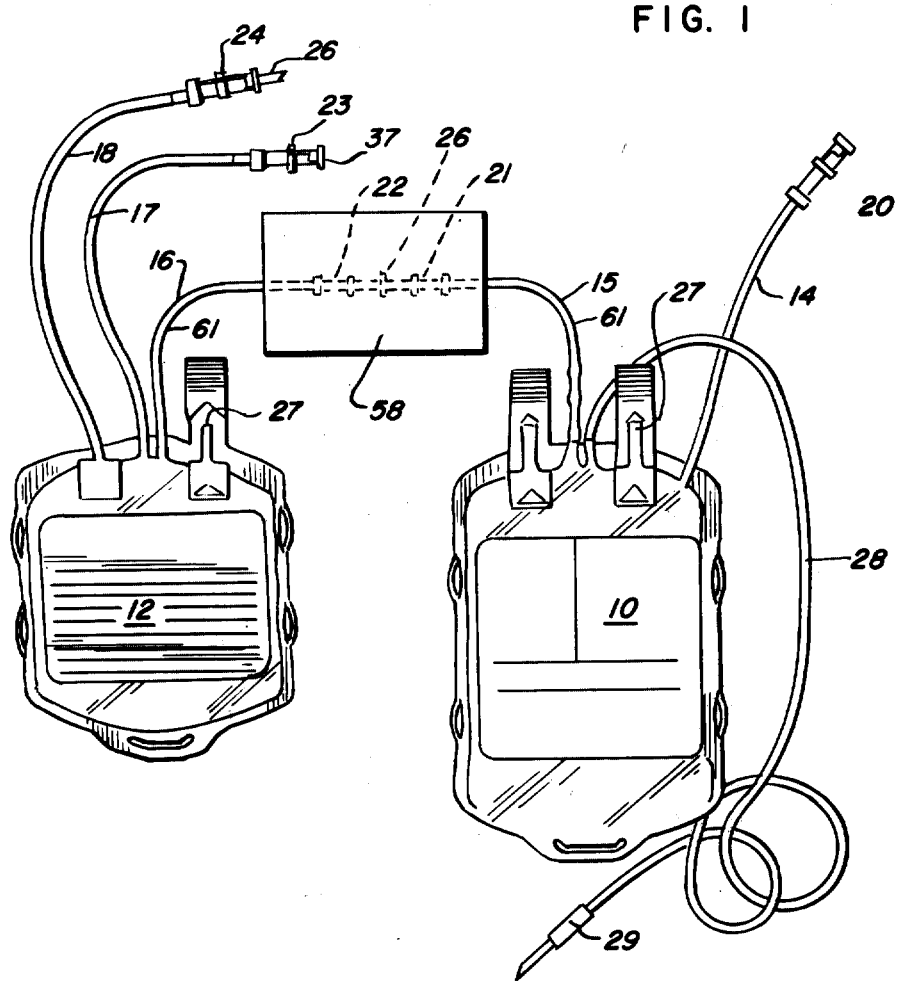
FIG. 1 is a plan view of a pair of blood bags incorporating sterile connectors made in accordance with this invention, and showing one of such connectors of one bag in connection with another said connector of the other bag.

In the specific embodiment of FIG. 1, a single blood collection bag 10 is shown in temporarily connected relationship through connector members 21, 22 with a single, transfer pack-type blood bag 12. However, it is contemplated that multiple-type bags, in which two or more blood bags are permanently connected together, may also carry fluid transfer tubes terminated with connector members; and it is further contemplated that any number of fluid transfer tubes and connector members may be placed upon blood bags or other containers as may be desired.

Blood bag 10 is shown to carry a conventional donor tube 28, which is terminated with a donor needle 29, for initial collection of blood from a donor. Access ports 27 are conventionally fabricated for administration of the blood through a conventional administration set.

When it is desired to make a sterile connection between two separate containers such as blood bags 10 and 12, one point of a double-pointed hollow spike 26 is inserted into each of the bores of connector members of the fluid transfer tubes of the separate containers. This is shown with connector members 21, 22, which define the free ends of fluid transfer tubes 15, 16.

Connector members 21, 22 each define a series of flanges 31, 33, 35, which are integrally molded therein. Each connector member defines a diaphragm 30 across its bore 32, said diaphragms being spaced from the free ends 37 of tubes 15, 16. Spike 26 is proportioned to tightly and sealingly fit into each bore 32.

Diaphragm 30 is positioned so that flanges 35 can abut against flange 34, mounted upon spike 26, without points 36 of spike 26 penetrates diaphragms 30. This is facilitated by the presence of a clip member 38, positioned between each flange 31 and 35 to prevent longitudinal collapse of the connector members 21, 22, with consequent rupture of the diaphragms by spike 26, until the clip members are removed.

Figure 4:
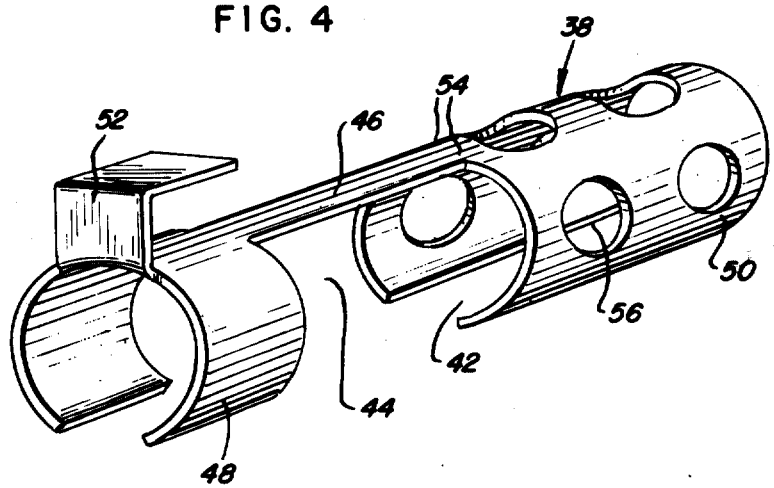
FIG. 4 is an enlarged, perspective view of a clip member shown in FIGS. 2 and 3.

Clip 38 is shown in detail in FIG. 4, and is a rigid, malleable structure made of brass or the like. Clip 38 is of hollow, cylindrical shape to define an axial, open slot 42 along the entire length thereof, to facilitate installation of the clip member on each connector member 20 through 24. A transverse, intermediately-located, cutaway portion 44 is provided in the generally cylindrical clip 38 to define a strip portion 46, connecting the respective generally cylindrical ends 48, 50 of the clip member. A tab portion 52 is located adjacent end 48, and is provided to permit end 48 to be bent at strip portion 46 away from the connector member that it surrounds, to permit the subsequent axial collapse of the connector member in the manner shown in FIG. 5. To facilitate the bending action, slits 54 are provided in strip 46.

If desired, apertures 56 may be provided in generally cylindrical portion 50 of the clip member.

Flange 33 on each of connector members 20 through 24 defines a slit or aperture 58, to permit the passage of strip 46 across it. Flanges 31 and 33 cooperatively restrain the major cylindrical end 50 of the clip member to position it, and to provide stability, as the minor cylindrical end 48 is pulled upwardly by tab 52, for opening of the structure.

The structure of this invention is used by first making the initial connection between two connector members (for example members 21 and 22) defining the ends of two fluid transfer tubes 15, 16, and a double-pointed spike 26, as shown in FIG. 2. Thereafter, the assembled connection between connector members 21, 22 and spike 36 is sterilized, typically by exposure to a brief cycle of dry heating in an electric oven (shown schematically in FIG. 1 at 58) at a temperature which is sufficient to kill all organisms. When connector members 20 through 24 are made of silicone rubber, there is no significant concern that a brief high temperature heating pulse will seriously degrade them. The silicone rubber also provides particularly good sealing characteristics in view of its highly hydrophobic nature, which prevents the migration of water droplets through the interface between spike 26 and silicone rubber connector members. A typical, dry-heating cycle which is believed to be suitable for most purposes is an application of temperature of 250° C. for about sixty seconds.

The sterilizing conditions must be applied to both diaphragms 30 of the connector members (as shown for example in FIG. 2) and to all of the structure in between, including spike 26, to create a sterile field on such inside portions of spike 26 and connector members 21, 22.

After the sterilization step is complete, tabs 52 are manipulated to cause ends 48 and strips 46 of clips 38 to bend upwardly about the line of weakness defined by slits 54, which is illustrated in FIG. 5. Thereafter, connector members 21, 22 can be axially collapsed, so that thin sections 60 thereof can bulge outwardly as shown in FIG. 5, thus shortening the distance between diaphragms 30. Accordingly, the diaphragms 30 are ruptured by ends 36 of spike 26, which establishes a sterile fluid connection between blood bags 10, 12. Accordingly, the contents of one of the bags, for example blood plasma formed upon centrifugation of bag 10, or a portion of the blood in bag 10, may be expressed from bag 10 through the connection thus formed into bag 12, without compromising the sterility of the system.

Thereafter, prior to disconnection of the structure shown in FIG. 5, fluid transfer tubes 15 and 16 may be sealed, for example at points 61 (FIG. 1) with a dielectric heat sealer or any other reliable means for maintenance of sterility. Then connector members 21, 22 may be disconnected from spike 26 to separate bags 10, 12.

Accordingly, a flexible system is provided in which separate, sterile, sealed containers may be connected in the manner described above for transfer of contents in sterile manner between originally separate containers.

The invention of this application can be used to permit separate blood bags to function in the manner that the present day multiple-blood bags function, with a high degree of versatility and flexibility of use.

Figure 6:
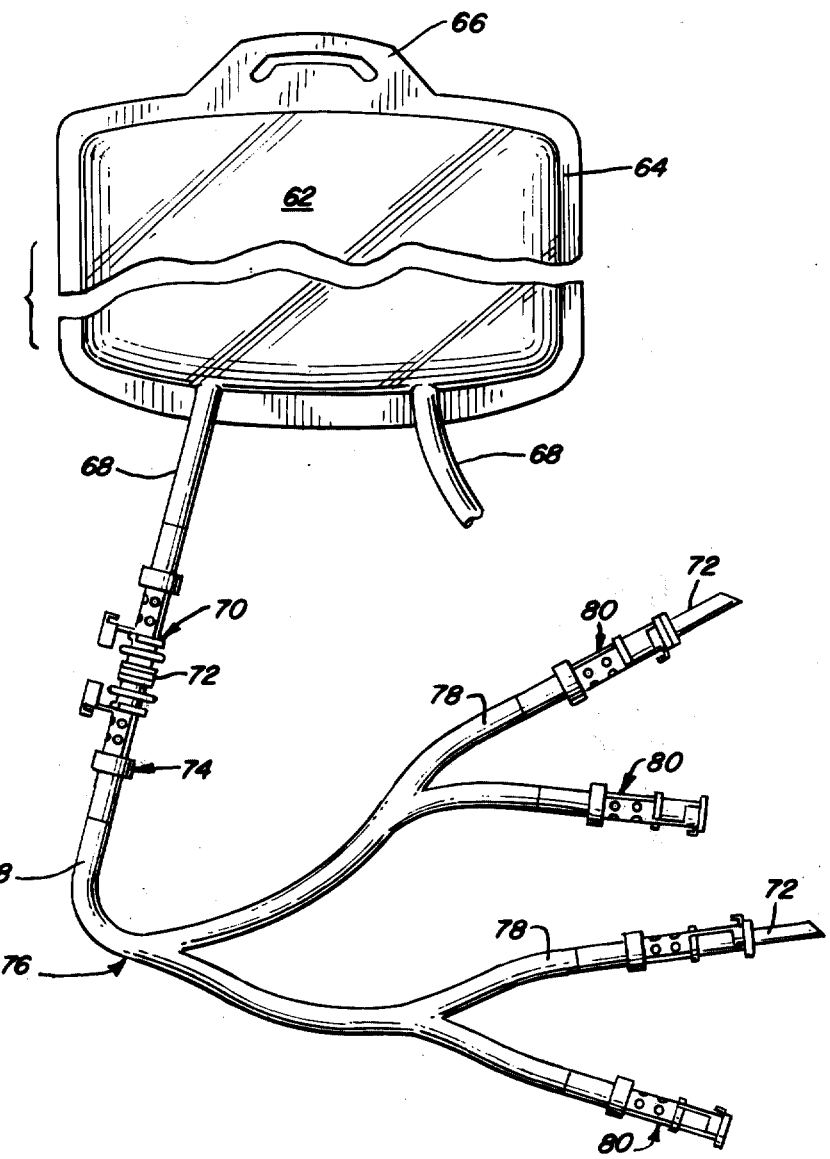
FIG. 6 is a plan view of a container with a large plurality of outlets and connector members, contemplated for use in dispensing a large number of separate portions of sterile fluid.

Turning to FIG. 6, a large container of sterile solution 62 is shown, being made of a pair of plastic sheets heat-sealed at the periphery 64, and having hangar means 66 at one end thereof. At its other end, a pair of fluid transfer tubes 67, 68 are provided. Fluid transfer tube 67 may communicate with a blood donor needle for collecting blood, or another blood bag, or may be terminated with a connector member of this invention, as desired. Tube 68 is also terminated with a connector member 70, of a structure similar to the previously described connector members. Spike 72 is shown to be positioned in the manner previously described in connector member 70, and to also be positioned in another connector member 74. Connector member 74 is carried by one end of a branching tubular flow set 76, which comprises as shown a branching array of connected tubular arms 78, each of which is terminated with a connector member 80 similar to the previously described connector members, some of which carry another double-pointed spike 72.

Accordingly, a sterile connection between container 62 and another container may be effected in the manner previously described. A sterile aliquot of solution may be provided through each arm 78 in this manner, for example for the repeated dispensing of sterile solution for the washing of glycerol from frozen blood cells. After dispensing of the desired amount of solution, the arm 78 involved in the specific dispensing operation is sealed, for example by means of a dielectric heat sealer. Thereafter, when another aliquot of solution is desired to be dispensed from container 62, another arm 78 is selected, and the sterile connection method described previously is performed once again for the dispensing of another aliquot of solution.

Branched-tube sets 76 are separate structures, but can be connected in sterile manner to sterile solution container 62, to provide an increased number of available connector members for future sterile connection. Accordingly, by this technique, solution container 62, and any other container having a single fluid transfer tube made in accordance with this invention, can be provided with any desired number of tube endings and connector members, for sterile connection in accordance with this invention.

The method of this invention may also be practiced with apparatus other than the preferred, double-pointed spike. For example, a single pointed spike may be permanently affixed to one fluid transfer tube, to rupture a diaphragm in another fluid transfer tube after the sterilization step. In this case, any desired design of seal can be used to seal the fluid transfer tube which carries the single-pointed spike, until after the sterilization step.

The above has been offered for illustrative purposes only, and is not for the purpose of restricting the invention of this application, which is as described in the claims below.

That which is claimed is:

1. The method of transferring sterile contents from a first, sealed, sterile container, having a first, flexible, sealed, fluid transfer tube, to a second, sealed, sterile container having a second, flexible, sealed, fluid transfer tube, said first and second tubes communicating at one end with their respective sealed, sterile containers, said first and second tubes having a free end, and being each sealed with a diaphragm across their bores, said diaphragms being spaced from the free ends of said first and second tubes, said method comprising:
    inserting one end of a double-ended, hollow spike into each of the bores of said first and second tubes at the free end thereof, said spike being proportioned to tightly and sealingly fit into each bore of the first and second tubes;
    sterilizing said spike and that portion of said first and second tubes extending from each said diaphragm to the free ends of said tubes; and thereafter
    axially collapsing said first and second tubes adjacent the free ends thereof to pass the ends of said spike through said diaphragms to open a flow channel between said first and second containers;
    transferring said sterile contents through said fluid transfer tubes from said first to said second container; and resealing said second fluid transfer tube while sterility is retained in said second tube.

2. The method of claim 1 in which the fluid transfer tubes are mechanically prevented from axial collapse to rupture said diaphragms, until after said sterilizing.

3. The method of claim 1 in which said first fluid transfer tube is resealed while sterility is retained therein.

4. A sealed sterile connection means between a first, sealed, sterile container having a sealed, flexible, sterile fluid transfer tube communicating at one end thereof with said first container and having a free end, and a second, sealed, sterile container having a second, sealed, flexible sterile fluid transfer tube communicating at one end thereof with said second container, and having a free end, said first and second fluid transfer tubes being each sealed with a diaphragm across their respective bores, said diaphragms being spaced from the free ends of said tubes, the improvement comprising:
    A double-ended, hollow spike, one end of said spike being inserted into each of the bores of said first and second tubes at the free ends thereof but spaced from said diaphragms to maintain the diaphragms intact, said spike being proportioned to tightly and sealingly fit into each bore of said first and second tubes, said first and second tubes being each sufficiently flexible adjacent their free ends to permit manual axial collapse thereof, to permit said diaphragms to be penetrated by the ends of said spike.

5. A sealed sterile connection means between a first, sealed, sterile container having a sealed, flexible, sterile fluid transfer tube communicating at one end thereof with said first container and having a free end, and a second, sealed, sterile container having a second, flexible, sterile fluid transfer tube communicating at one end thereof with said second container and having a free end, said first and second fluid transfer tubes being each sealed with a diaphragm across their respective bores, said diaphragms being spaced from the free ends of said tubes, the improvement comprising:

a double-ended, hollow spike, one end of said spike being inserted into each of the bores of said first and second tubes at the free ends thereof, but spaced from said diaphragms to maintain the diaphragms intact, said spike being proportioned to tightly and sealingly fit into each bore of said first and second tubes, said first and second tubes being each sufficiently flexible adjacent their free ends to permit manual axial collapse thereof, to permit said diaphragms to be penetrated by the ends of said spike, and removable clip members surrounding each said fluid transfer tube adjacent each free end, to prevent said axial collapse, and consequent rupturing of the diaphragms of said tubes, by said hollow spike prior to removal of said clip member in which the free end of said sealed, flexible tube is provided with a first external flange adjacent its free end and a second external flange positioned on said tube adjacent said diaphragm, said clip member being positioned in an abutting relationship between said first and second flanges.

6. The connection means of claim 5 in which the free end of each said flexible, sealed tube comprises a tubular connector member having a first external flange about its free end and a second external flange positioned on said tube near said diaphragms, and said clip members are positioned between said first and second flanges to facilitate the prevention of said axial collapse.

7. The connection means of claim 6 in which a portion of each said tube adjacent said clip member is of reduced thickness to facilitate axial collapse when said clip member is removed.

8. The connection means of claim 7 in which said clip member defines a rigid, malleable structure of hollow cylindrical shape, said structure defining an axial, open slot along the entire length thereof to facilitate the installation and removal of said clip member; a transverse, intermediately located cutaway portion, to define a strip portion connecting the respective ends of said clip member; a tab portion being located adjacent one end thereof, whereby the end of said clip member which carries the tab portion may be bent about said strip portion away from said connector member to permit the axial collapse thereof.

9. The connection means of claim 8 in which said connector member defines a partial flange having a longitudinal opening defined therethrough, said partial flange being located intermediate said first and second flanges on the exterior of said tube, said strip member of the clip member being positioned in said opening.

10. The device of claim 9 in which said first and second containers are plastic blood bags.

11. The device of claim 9 in which said connector member includes said diaphragm, and is made of silicone rubber.

12. The sealed sterile connection means of claim 5 in which the free ends of said first and second fluid transfer tubes are of identical shape.

13. A sealed, sterile container having a sealed, flexible, sterile fluid transfer tube communicating at one end thereof with said container and having a free end; the improvement comprising:

a diaphragm positioned across the bore of said tube, said diaphragm being spaced from the free end thereof, said tube being sufficiently flexible to permit manual axial collapse thereof adjacent said free end, and a removable clip member surrounding said fluid transfer tube adjacent the free end thereof, to prevent said axial collapse prior to removal of said clip member.

14. The sealed sterile container of claim 13 including a double-pointed hollow spike, one point of said spike being inserted in the bore of said fluid transfer tube at the free end thereof, but spaced from said diaphragm, said spike being proportioned to tightly and sealingly fit into the bore of said free end, whereby, upon connection of the other point of said spike into the bore of another sealed, flexible, fluid transfer tube, and subsequent sterilization, a sterile path may be provided by axially collapsing said fluid transfer tube so that the spike ruptures the diaphragm.

15. The sterile container of claim 13 which is a blood bag.

16. The sterile container of claim 13 which is a bag for physiological solution and which carries a plurality of flexible, sealed fluid transfer tubes.

17. The sealed, sterile container of claim 13 in which said free tube end comprises a tubular connector member which includes said diaphragm, said connector member being made of silicone rubber.

18. The sealed, sterile container of claim 17 in which a portion of said tubular connector member is of reduced thickness to facilitate the axial collapse, when said clip member is removed.

19. The sealed, sterile container of claim 18 in which said clip member defines a rigid, malleable structure of hollow cylindrical shape, said structure defining an axial, open slot along the entire length thereof to facilitate the installation and removal of said clip member; a transverse, intermediately located cutaway portion, to define a strip portion connecting the respective ends of said clip member; a tab portion being located adjacent one end thereof, whereby the end of said clip member which carries the tab portion may be bent about said strip portion away from said connector member, to permit the axial collapse thereof.

20. The sealed, sterile container of claim 19 in which said connector member defines a partial flange having a longitudinal opening defined therethrough, said partial flange being located intermediate said first and second flanges on the exterior of said connector member, said strip member of the clip member being positioned in said opening.

* * * * *